US005687714A

United States Patent [19]
Kolobow et al.

[11] Patent Number: 5,687,714
[45] Date of Patent: Nov. 18, 1997

[54] SELF-CLEANING ENDOTRACHEAL TUBE APPARATUS

[75] Inventors: Theodor Kolobow, Rockville; Rudolf Trawoger, Bethesda, both of Md.

[73] Assignee: The United States of America as represented by the Department of Health and Human Services, Washington, D.C.

[21] Appl. No.: 541,846

[22] Filed: Oct. 10, 1995

[51] Int. Cl.$^6$ ................................................ A61M 16/00
[52] U.S. Cl. .............................. 128/207.14; 128/201.11; 128/203.16; 128/204.14
[58] Field of Search ................ 128/200.11, 200.16, 128/203.12, 203.16, 204.14, 207.14, 207.15

[56] References Cited

U.S. PATENT DOCUMENTS

| | | | |
|---|---|---|---|
| 4,646,733 | 3/1987 | Stroh et al. | 128/207.16 |
| 4,770,168 | 9/1988 | Rusz et al. | 128/203.12 |
| 5,186,167 | 2/1993 | Kolobow | 128/207.14 |
| 5,226,411 | 7/1993 | Levine | 128/203.26 |
| 5,231,983 | 8/1993 | Matson et al. | 128/207.15 |
| 5,291,882 | 3/1994 | Makhoul et al. | 128/207.15 |
| 5,452,715 | 9/1995 | Boussignag | 128/207.14 |
| 5,487,378 | 1/1996 | Robertson et al. | 128/200.16 |

FOREIGN PATENT DOCUMENTS

| | | |
|---|---|---|
| WO 86/02566 | 5/1986 | WIPO . |
| WO94/01157 | 1/1994 | WIPO . |
| WO 94/03225 | 2/1994 | WIPO . |

OTHER PUBLICATIONS

Kolobow, M.D. T., Powers, T., Mandava, M.D. S., et al. *Anasthesia Analg*, 78:455–461 (1994).

Hickling, K.G., *Intensive Care Med.*, 16:219–226 (1990)

*Primary Examiner*—Aaron J. Lewis
*Attorney, Agent, or Firm*—Townsend and Townsend and Crew LLP; Guy W. Chambers

[57] ABSTRACT

An endotracheal tube apparatus (10) which can efficiently impart air to the lungs of a human or animal while preventing the harmful build up of mucus deposits on critical parts of the apparatus. This endotracheal tube apparatus features an endotracheal tube (12) and a catheter (14) which are together inserted into the trachea (16) of a human or animal to a point slightly above the carina (28) of the lungs. Humidified air entrained with water or saline droplets from reservoir (56) is pumped into and through the catheter. The catheter features a reverse thrust catheter (RTC) tip (60, 62, 64, 80) at its distal end (24) which reverses the direction of humidified air flow away from the lungs. The RTC tip serves to protect the lungs from accumulation of water or saline droplets while the water or saline droplets continually clean both the catheter and endotracheal tube by dissolving and expelling any mucus which might otherwise accumulate.

13 Claims, 4 Drawing Sheets

SELF-CLEANING ENDOTRACHEAL TUBE APPARATUS

TECHNICAL FIELD OF THE INVENTION

The present invention relates to medical devices used to assist breathing. More particularly, an endotracheal tube apparatus is disclosed which can safely and efficiently impart air and oxygen to the lungs while preventing the harmful build up of encrusted mucus deposits on critical parts of the apparatus.

BACKGROUND OF THE INVENTION

Through injury or diseases, such as pneumonia or congenital diaphragmatic hernia (CDH), human or animal lungs can become too weak to themselves sustain a sufficient flow of oxygen to the body and to remove adequate amounts of carbon dioxide. Under these conditions, it is often necessary to aid the lungs through forms of mechanical assistance, such as intratracheal ventilation (ITV).

In its simplest form, ITV involves the introduction of an endotracheal tube and a small, open ended catheter within that tube into the trachea of a human or animal. The distal ends of the endotracheal tube and catheter are positioned to rest at or near the carina of the lungs. A well-humidified oxygen/air mixture is then introduced through the catheter to provide oxygen more directly to the lungs. Through this arrangement of a catheter and endotracheal tube, the distance between the source of oxygen (i.e., the mouth vs. the distal end of the catheter) and the lungs is significantly reduced. By reducing this distance or "anatomical dead space" between the mouth and carina, less lung strength is required to obtain the oxygen necessary for the body to function and for carbon dioxide to be removed from the lungs.

Using this "simplest form" of ITV equipment to assist the lungs nonetheless gives rise to a number of problems. Perhaps the most serious of these problems occurs when water droplets are entrained in the ITV air stream and allowed to pass out the open end of the catheter and directly into the lungs. Such water droplets can then collect in the lungs with potentially serious consequences. Up to this point, the water entrainment problem has been addressed by carefully preparing the air stream so that it carries no entrained water droplets. This is often done, for example, by inserting filters in the air line to trap entrained water.

A second problem, which is addressed in the inventor's previous U.S. Pat. No. 5,186,167, involves the damage to the lungs and additional dead space which can be created by air shooting out the open end of a catheter and into the lungs at high peak airway pressures (HPAP). Such a jet stream of air has a tendency to overinflate the lungs. To overcome this problem, different configurations of diffusers were disclosed which could be placed at the distal end of the catheter to break up this jet stream of air.

A third problem with commonly used ITV equipment is the collection of mucus on the catheter and endotracheal tube. In a healthy human or animal, mucus secretions are removed from the lungs and the trachea by the mucociliary action of the epithelial cells and through coughing. This mucus removal mechanism is generally not available, though, to an intubated patient. Instead, for an intubated patient, the mucus in the trachea and lungs has a tendency to collect on the surface of both the catheter and endotracheal tube to then dry to become a crusty film as air is continually passed across it. As this encrusted mucus accumulates on the catheter, it begins to clog them. This accumulation of encrusted mucus also can promote harmful bacterial growth.

To overcome this mucus accumulation problem, the catheter frequently needs to be removed and cleaned. The frequent removal, cleaning and reinsertion of the catheter involves significant inconvenience to the patient and health care worker as well as the dangers associated with interruption of patient ventilation.

SUMMARY OF THE INVENTION

The present invention provides an endotracheal tube apparatus which can efficiently impart air to the lungs while preventing the harmful build up of mucus deposits on critical parts of the apparatus. This endotracheal tube apparatus features an endotracheal tube and a catheter, with a reverse thrust catheter (RTC) tip, within the endotracheal tube. Typically, the catheter is used to bring fresh air into the lungs while the endotracheal tube is used to allow stale air to be removed from the lungs. The RTC tip functions to reverse the flow of air coming through the catheter so that such air flow is no longer directed at the lungs. Together, the endotracheal tube and catheter are inserted to a point slightly above the carina of the lungs and supplied with humidified air into which a small amount of water droplets are entrained. For many applications, the humidified air can consist of a mixture of room air and oxygen which has been passed through a humidifier. Water droplets can be added to this humidified air either through a micropump or a bubbler. By using a reverse thrust catheter and carefully controlling the amount of water which is entrained in the humidified air, the entrained water will be used beneficially to dissolve and expel mucus which collects both on the catheter and endotracheal tube rather than allowing water to harmfully collect in the lungs.

DESCRIPTION OF THE SPECIFIC EMBODIMENTS

Figure 1:
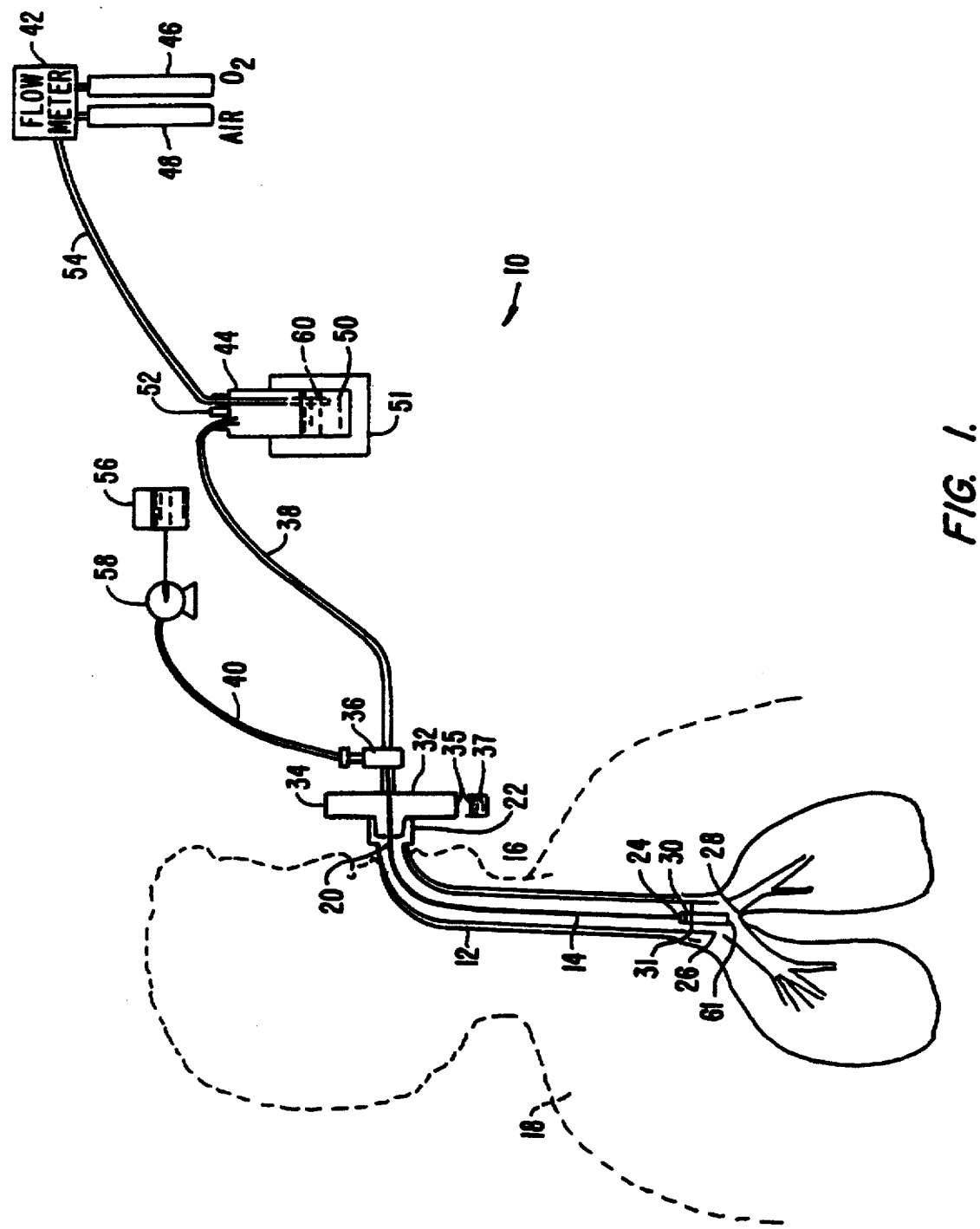
FIG. 1 shows a schematic view of a preferred embodiment of endotracheal apparatus for the present invention.

FIG. 1 shows a preferred form of endotracheal tube apparatus 10 for the present invention. This endotracheal apparatus 10 features an endotracheal tube 12 and a tubular catheter 14 which is concentrically fitted within the endotracheal tube 12. Both the endotracheal tube 12 and catheter 14 are preferably formed of a flexible plastic, such as polyvinylchloride (PVC) or silicone rubber, which is suitable for insertion into the trachea 16 of a human 18. For an adult human 18, a PVC catheter 14 of 3.4 mm outside diameter and 2.64 mm inside diameter has often been found to be suitable to sustain the desired air flow rates. The endotracheal tube 12 should be of a diameter which fits comfortably against the inner surface of the trachea 16.

Both the catheter 14 and endotracheal tube 12 should be long enough to reach from the point of entry into the human body at their proximal ends 20, 22 to a point which is slightly above (i.e., approximately 1 cm) the carina 28 of the lungs at their distal ends 24, 26. To help correctly position the distal ends 24, 26 of the catheter 14 and endotracheal tube 12 slightly above the carina, a detectable marker 30, 31, such as a radio opaque tantalum band, is preferably embedded in both the catheter's distal end 24 and endotracheal tube's distal end 26. These detectable markers 30, 31 can be monitored with x-rays and roentgenographic films. The point of entry into the human body for the catheter 14 and endotracheal tube 12 can vary depending upon the application. For example, common points of entry include the patient's nose, mouth or throat (i.e., resulting from a tracheostomy).

At its proximal end 22, the endotracheal tube 12 is preferably attached to a T-piece connector 32. This T-piece connector 32 has ports 34, 35 to which mechanical ventilation devices can be attached to further help with the inspiration and expiration of air. For example, a mechanical ventilator to assist inspiration, such as a balloon ventilator (not shown), can be attached to port 34 to provide a continuous positive airway pressure (CPAP). A mechanical regulator to assist expiration can be attached to port 35 to provide a positive end expiratory pressure (PEEP). The port 35 can also be used to allow dissolved mucus which is expelled from the endotracheal tube 12 to collect in a suitable receptacle, such as glass beaker 37. The catheter 14 would typically pass through the T-piece connector 32 until it reaches the catheter connector 36.

At catheter connector 36, humidified air from flexible tubing 38 is mixed with water droplets from flexible tubing 40. As with the catheter 14 and endotracheal tube 12, the external tubing 38, 40 should be made from a flexible plastic such as polyvinylchloride (PVC), silicone rubber or polytetrafluoroethylene (PTFE or TEFLON®). In order to ensure that the temperature of air/water mixture is kept at an appropriate level, flexible tubing 38 should be clad with insulating material, such as multiple layers of a thin plastic wrap.

Humidified air is supplied to flexible tubing 38 from flow meter 42 and humidifier 44. Typically, the flow meter 42 will mix air and oxygen at room temperature. Both the air and oxygen can advantageously be stored in compressed form in tanks 46, 48 to allow the quality, flow rate and composition of the mixture to be carefully controlled. The air to oxygen content of the mixture can be adjusted by flow meter 42 as needed to range from 100% air to 100% oxygen. Usually, oxygen content will be adjusted from 0% to 80% of the mixture.

The endotracheal tube apparatus 10 of the present invention can be operated at a variety of different flow rates. As a guide to selecting an appropriate flow rate, the following suggestive correlation between respiratory rate, flow rate and pressure is provided for an adult human:

| Respiratory Rate | Flow Rate | Pressure |
| --- | --- | --- |
| 20/min | 4.8 liters/min | 3 psi |
| 40/min | 9.6 liters/min | 6 psi |
| 60/min | 14.4 liters/min | 10 psi |
| 80/min | 19.2 liters/min | 15 psi |

After air and oxygen are mixed at flow meter 42, the mixture is sent to a humidifier 44 through plastic supply tubing 54 to be humidified. This humidifier is typically composed of a reservoir 50 partially filled with sterile water and heated by suitable means, such as an electrical heater 51, to a temperature of about 37°–40° C. A cover 52 is affixed to the top of the reservoir 50 to prevent contamination of the sterile water and allow tubes 38 and 54 to access the reservoir. In operation, the air/oxygen mixture coming from the flow meter 42 will flow into the reservoir above the heated water and mix with water vapors. After this mixture becomes humidified with the water vapors, it leaves the humidifier 44 through tubing 38.

To entrain water droplets in the humidified air coming from the humidifier 44, a second reservoir 56 of sterile water or saline solution is provided from which micropump 58 pumps liquid at the appropriate rate. For a humidified air flow rate of 15 liters per minute, it has been found that 1 drop of water or saline per minute (i.e., 0.10 ml/min) is a suitable amount to add to the humidified air. The mucus clearing effects of adding water or saline to the humidified air seem to be more pronounced at higher flow rates, such as 12–18 liters per minute.

As an alternative to the reservoir 56 and micropump 58 shown in FIG. 1, water droplets can be entrained in the humidifier 44 by extending the outlet 60 of the air/oxygen input tube 54 below the reservoir 50 water level. By so extending the tubing 54, a "bubbler" will be created in the reservoir 50. Nonetheless, this approach to entraining water in the humidified air is less preferred because it is more difficult to control the amount of water which is being entrained. If too many water droplets are entrained in the humidified air, these water droplets may begin to be deposited in the lungs rather than simply clearing away mucus on the catheter and endotracheal tube.

It is believed that the entrained water droplets keep the endotracheal tube 12 and catheter 14 clean by dissolving mucus the droplets come in contact with and allowing the dissolved mucus to be easily expelled through the endotracheal tube 12. In the absence of such droplets, the mucus will dry and harden around the catheter and endotracheal tube surfaces, particularly at their distal end 24, 26.

To achieve self-cleaning operation without allowing water to collect in the lungs, it is important to have an appropriate catheter tip 61 at the distal end 24 of the catheter 14. Preferred forms of catheter tips 61 for the present invention are the reverse thrust catheter (RTC) tips 62, 64, 80 shown in FIGS. 2A–B, 3A–B and 4. These types of catheter tips 62, 64, 80 are designed to direct the flow of air, oxygen and entrained water droplets exiting from the distal end 24 of the catheter away from the carina 28 of the lungs. Accordingly, gas exit ports 66, 68, 78 of these RTC tips 62, 64, 80 face away from the carina 28 and toward the proximal end 20 of the catheter 14. The RTC tips 62, 64 are preferably formed of a medically suitable plastic, such as nylon, polyvinylchloride (PVC), silicone rubber or polytetrafluoroethylene (PTFE or TEFLON®), and can be made as an integral part of the catheter 14. Alternatively, the RTC tips 62, 64 can be affixed to the catheter through plastic welding or a medically acceptable adhesive.

Figure 2A:
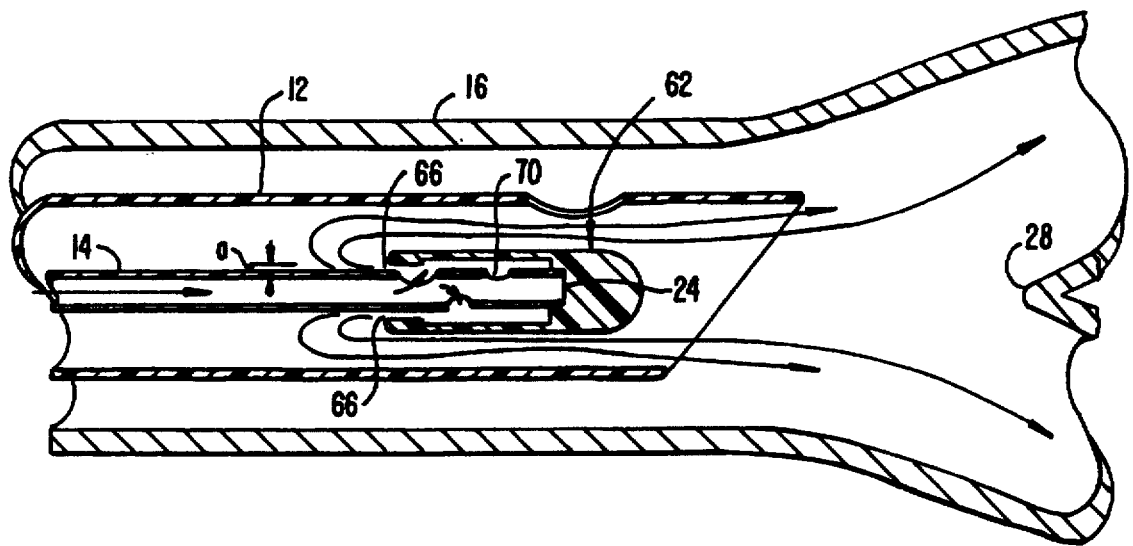
FIG. 2A shows a side view of a preferred form of reverse thrust catheter tip during patient inspiration.
Figure 2B:
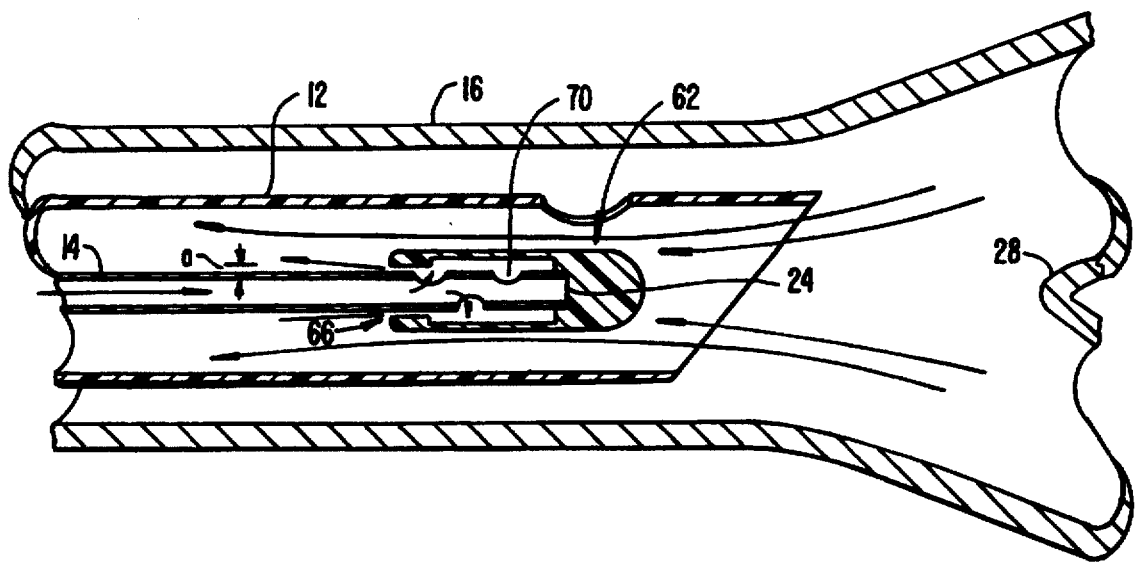
FIG. 2B shows a side view of the same preferred form of reverse thrust catheter tip as FIG. 2A but during patient expiration.
Figure 3A:
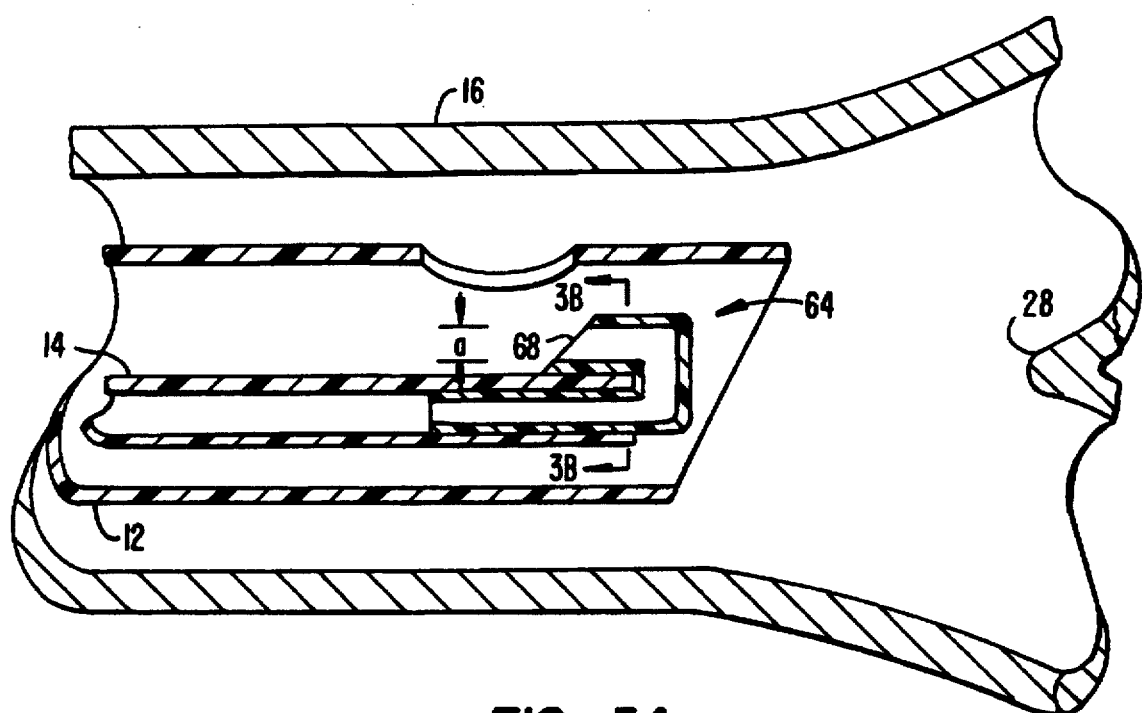
FIG. 3A shows a side view of an alternative form of reverse thrust catheter tip.
Figure 3B:
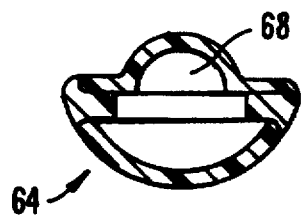
FIG. 3B shows a section view of the alternative form of reverse thrust catheter tip shown in FIG. 3A.
Figure 4:
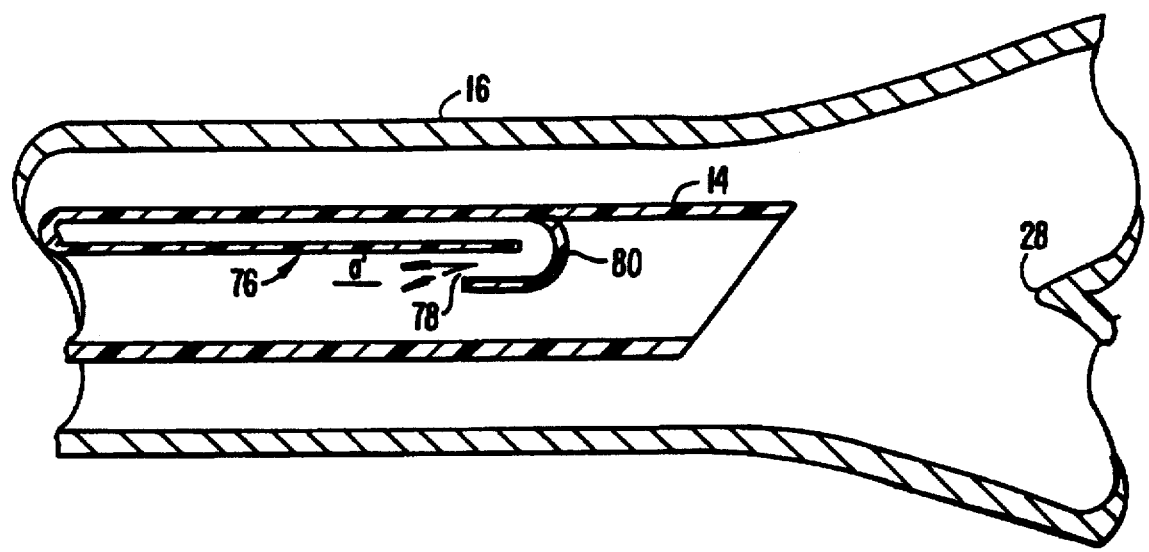
FIG. 4 shows a side view of a catheter and reverse thrust catheter tip which are formed as an integral piece of the endotracheal tube.

Comparing the RTC tips 62, 64 from FIGS. 2A–B, 3A–B and 4, it is clear that there are a number of ways of directing flow away from the carina 28. For example, FIGS. 2A–B shows that the air/oxygen flow can first be diffused through holes 70 at the distal end 24 of the catheter 14 and then directed away from the carina through an annular opening 66 in the catheter tip 62. As an alternative embodiment, FIGS. 3A–B show that a hook-like configuration of catheter tip 64 can be used to achieve a similar result. FIG. 4 illustrates how the catheter 76 and catheter tip 80 can even be formed as an integral part of the endotracheal tube 14 using a similar hook-like configuration for the catheter tip 80.

For these types of RTC tips 62, 64, 80, the width of gap "a" in the exit ports 66, 68, 78 determines the flow-pressure characteristics at the level of the carina for any given flow rate. The gap "a" should preferably be kept small, for example between 0.005 and 0.020 inches, to create a venturi effect at the carina. Without the entrained water droplets of the present invention, such small catheter tip exit ports 66, 68, 78 have a tendency to become clogged with dried mucus. By adding water droplets to the humidified air, though, any mucus which collects at these exit ports is usually dissolved and expelled.

To use the self-cleaning endotracheal tube apparatus 10 of the present invention for a human or animal patient, the endotracheal tube 12 and catheter 14 are first inserted into an appropriate patient orifice leading to the lungs, such as the patient's mouth. To prevent bunching or kinking of the catheter, a guide wire (not shown) can be placed in the catheter to help steer the catheter until the catheter has reached its operational position. The positioning of the endotracheal tube 12 and catheter 14 can be checked using x-rays and roentgenographic films. When the endotracheal tube 12 and catheter 14 are correctly positioned, the detectable markers 30, 31 should indicate that the distal ends 24, 26 of both are slightly above the patient's carina 28.

After the endotracheal tube 12 and catheter 14 have been correctly inserted, they can then be attached to the remaining equipment for supplying humidified air to the patient, including the T-piece connector 32, humidifier 44 and catheter connector piece 36. A proper air/oxygen mixture and flow rate, such as 15 liters per minute, should be set at the flow meter 42 with an accompanying rate of pumped water, such as one drop per minute, set at the micropump 58. Having made the proper setting, the endotracheal tube apparatus 10 can be used to assist patient ventilation in a self-cleaning manner.

As known by those of skill in the art, a number of variations to the mechanically assisted ventilation technique described here can be employed with the endotracheal tube apparatus 10 of the present invention. For example, for intratracheal pulmonary ventilation (ITPV), all the fresh air and oxygen is introduced through the catheter 14. The endotracheal tube 12 is used for expiration only. The expiration though this endotracheal tube 12 is controlled by an expiratory valve (not shown) which is attached, for example, to port 35 of the endotracheal T-piece connector 32. When the expiration valve is closed, all of the air and oxygen from the catheter 14 enters the lungs as shown, for example, in FIG. 2A. When the expiratory valve is open, all of the air and oxygen from the lungs plus the continuous flow from the catheter 14 is exhaled through the endotracheal tube as shown, for example, in FIG. 2B. As alternatives to this intratracheal pulmonary ventilation (ITPV) technique, a continuous positive airway pressure (CPAP) can be supplied through the endotracheal tube 12 or a regulator (not shown) at catheter connector piece 36 can be used to make the flow of air and oxygen through the catheter 14 intermittent.

In the foregoing specification, the invention has been described with reference to specific preferred embodiments and methods. It will, however, be evident to those of skill in the art that various modifications and changes may be made without departing from the broader spirit and scope of the invention as set forth in the appended claims. The specification and drawings are, accordingly, to be regarded in an illustrative, rather than restrictive, sense; the invention being limited only by the appended claims.

What is claimed is:

1. An apparatus for intratracheal ventilation of human or animal lungs comprising:

an endotracheal tube for insertion into a human or animal trachea to a point above a human's or animal's lungs;

a catheter positioned within said endotracheal tube, having proximal and distal ends;

a source of humidified air flow connected to the proximal end of said catheter to provide humidified air flow through said catheter;

means to entrain liquid droplets to said humidified air flow so that the air flow in said catheter consists of humidified air with entrained liquid droplets, said liquid droplets being entrained in an amount sufficient to detectably dissolve mucus deposits on said catheter and within said endotracheal tube while not producing a significant accumulation of water in a human's or animal's lungs; and, a flow-reversing catheter tip affixed to the distal end of said catheter having an exit port directed away from a human's or animal's lungs.

2. The intratracheal ventilation apparatus of claim 1 wherein approximately 1 drop of water is entrained every minute.

3. The intratracheal ventilation apparatus of claim 1 wherein said catheter and flow-reversing catheter tip are formed as an integral part of said endotracheal tube.

4. The intratracheal ventilation apparatus of claim 1 wherein said source of humidified air includes:

a compressed oxygen tank;

a compressed air tank;

a flow meter connected to said oxygen and air tanks to mix oxygen and air in desired proportions; and, a humidifier connected to said flowmeter to humidify the mixture of oxygen and air received from the flow meter.

5. The intratracheal ventilation apparatus of claim 1 wherein said liquid droplets are sterile water.

6. The intratracheal ventilation apparatus of claim 1 wherein said liquid droplets are saline solution.

7. An apparatus for intratracheal ventilation of human or animal lungs comprising:

an endotracheal tube for insertion into a human or animal trachea to a point above a human's or animal's lungs;

a catheter positioned within said endotracheal tube, having proximal and distal ends;

a source of humidified air flow connected to the proximal end of said catheter to provide humidified air flow through said catheter;

means to entrain liquid droplets to said humidified air flow so that the air flow in said catheter consists of humidified air with entrained liquid droplets, said means to entrain including:

a reservoir of sterile water;

a pump for pumping water from said reservoir; and, a connector piece operably connected to said pump and said catheter for pumping water droplets into the humidified air passing through said catheter; and, a flow-reversing catheter tip affixed to the distal end of said catheter having an exit port directed away from a human's or animal's lungs.

8. A method for self-cleaning intratracheal ventilation of a human or animal comprising the steps of:

selecting an endotracheal tube, with proximal and distal ends, which can comfortably be inserted into a human's or animal's trachea;

selecting a catheter, with proximal and distal ends, to fit within said endotracheal tube;

affixing a flow-reversing tip onto the distal end of said catheter which is capable of reversing the direction of air flow as the air exits said catheter;

inserting both said endotracheal tube and said catheter into a human or animal's trachea until their distal ends reach a selected point above a human's or animal's lungs;

attaching the proximal end of said catheter to source of humidified air into which liquid droplets are entrained, said liquid droplets being entrained in an amount sufficient to detectably dissolve mucus deposits on said catheter and within said endotracheal tube while not producing a significant accumulation of water in a human's or animal's lungs; and, infusing a mixture of humidified air and oxygen into a human's or animal's lungs through said catheter.

9. The method for self-cleaning intratracheal ventilation of claim 8 wherein said liquid droplets consist of sterilized water.

10. The method for self-cleaning intratracheal ventilation of claim 8 wherein said liquid droplets consist of saline.

11. The method for self-cleaning intratracheal ventilation of claim 9 wherein 1 drop of water is entrained for every 15 liters of air flow.

12. The method for self-cleaning intratracheal ventilation of claim 8 wherein the selected point above the lungs is 1 cm above the carina of the lungs.

13. The method for self-cleaning intratracheal ventilation of claim 8 further including the step of affixing detectable markers to the distal end of said endotracheal tube and said catheter to allow their insertion to a selected point above the lungs to be confirmed with x-rays.

* * * * *